US011011367B2

United States Patent
Shinoda et al.

(10) Patent No.: US 11,011,367 B2
(45) Date of Patent: May 18, 2021

(54) LIGHT-EMITTING TUBE ARRAY-TYPE LIGHT SOURCE DEVICE

(71) Applicant: SHIKOH TECH CO., LTD, Awaji (JP)

(72) Inventors: Tsutae Shinoda, Akashi (JP); Hitoshi Hirakawa, Takasago (JP); Kenji Awamoto, Miki (JP); Takefumi Hidaka, Kobe (JP); Junichiro Takahashi, Nishinomiya (JP); Tetsuya Makino, Kakogawa (JP)

(73) Assignee: SHIKOH TECH CO., LTD., Awaji (JP)

( * ) Notice: Subject to any disclaimer, the term of this patent is extended or adjusted under 35 U.S.C. 154(b) by 0 days.

(21) Appl. No.: 16/592,062

(22) Filed: Oct. 3, 2019

(65) Prior Publication Data

US 2020/0152442 A1  May 14, 2020

(30) Foreign Application Priority Data

Nov. 12, 2018 (JP) .............................. JP2018-212244
May 27, 2019 (JP) .............................. JP2019-098612

(51) Int. Cl.
| H01J 65/04 | (2006.01) |
| H01J 61/06 | (2006.01) |
| H01J 61/30 | (2006.01) |
| H01J 61/92 | (2006.01) |
| H01J 61/33 | (2006.01) |

(52) U.S. Cl.
CPC .............. *H01J 65/04* (2013.01); *H01J 61/06* (2013.01); *H01J 61/305* (2013.01); *H01J 61/33* (2013.01); *H01J 61/92* (2013.01)

(58) Field of Classification Search
None
See application file for complete search history.

(56) References Cited

U.S. PATENT DOCUMENTS

| 2004/0033319 A1* | 2/2004 | Yamada ................... H01J 9/20 427/558 |
| 2017/0186596 A1 | 6/2017 | Shinoda et al. |
| 2018/0144925 A1 | 5/2018 | Shinoda et al. |

FOREIGN PATENT DOCUMENTS

| JP | 2017-027912 A | 2/2017 |
| WO | 2016/125708 A1 | 4/2017 |
| WO | 2017/094483 A1 | 9/2018 |

* cited by examiner

*Primary Examiner* — Ashok Patel
(74) *Attorney, Agent, or Firm* — Stites & Harbison, PLLC; Jeffrey A. Haeberlin; Gary N. Stewart (57) ABSTRACT

A light-emitting tube array-type light source device includes: a plurality of light-emitting gas discharge tubes 11; and an electrode substrate 30 supporting the light-emitting gas discharge tubes in parallel on an upper surface thereof, the electrode substrate having a plurality of slits partially exposes a bottom surface of each light-emitting tube, thereby the light-emitting gas discharge tubes can be cooled through the slits.

13 Claims, 8 Drawing Sheets

LIGHT-EMITTING TUBE ARRAY-TYPE LIGHT SOURCE DEVICE

CROSS-REFERENCE TO RELATED APPLICATION

This application claims priority from prior Japanese Patent Applications No. 2019-98612 filed on May 27, 2019 and No. 2018-212244 filed on Nov. 12, 2018, the entire contents of which are incorporated herein by reference.

BACKGROUND OF THE INVENTION

Field of the Invention

The present invention relates to a light-emitting tube array-type light source device and a light source module using the same, and especially relates to a deep ultraviolet light emitting light source device configured to have a plurality of gas discharge light-emitting tubes formed of glass tubes arranged in parallel to each other. Also, the present invention proposes a new fluid treatment device for sterilization or deodorization by applying the deep ultraviolet light-emitting light source device.

Description of the Related Art

In recent years, a light-emitting tube array-type light source device utilizing gas discharge has been proposed in related art documents D1-D3 as mentioned below. The light source device comprises: a plurality of gas discharge light-emitting tubes mainly made of glass tubes, the tubes enclosing a discharge gas therein; and an electrode substrate supporting the light-emitting tubes arranged in parallel to each other.

Figure 1A:
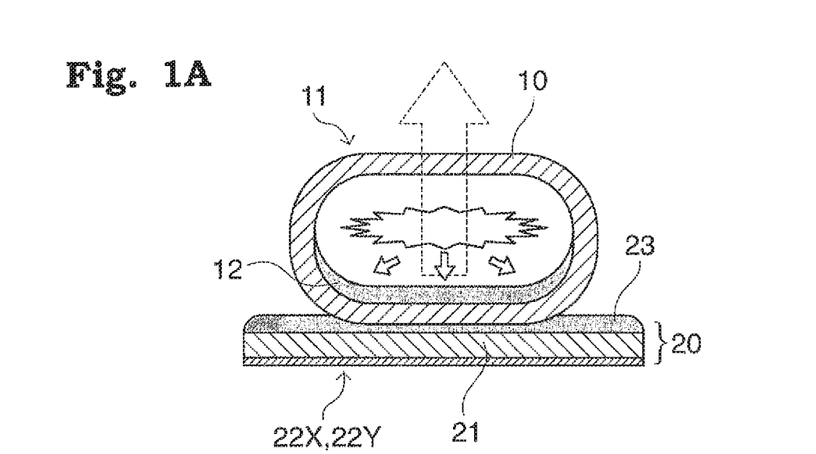
FIG. 1A illustrates a cross-section view of a gas discharge light-emitting tube as a unit light-emitting element.

FIG. 1A illustrates a transverse cross-section view of a gas discharge light-emitting tube as a unit light-emitting element. A gas discharge light-emitting tube 11 is formed of a glass tube 10 in the form of a flat-oval cross-section. The light-emitting tube 11 encloses a gas of neon (Ne), argon (Ar), krypton (Kr), helium (He), xenon (Xe) or mixed noble gases, such as Ne and Xe, Ne and Xe, He and Xe or Ar and Xe, and other gases therein that emits ultraviolet light. The light-emitting tube 11 has an ultraviolet phosphor layer or a reflecting layer 12 formed on an inner bottom surface thereof, the ultraviolet phosphor layer 12 emitting ultraviolet light when excited by vacuum ultraviolet light from gas discharge. In the case that the layer 12 comprises a reflecting material such as a magnesium oxide (MgO), the reflecting layer 12 reflects the vacuum ultraviolet light from gas discharge to a front surface side. The light-emitting tube 11 lies on an electrode substrate 20 placed opposite to an outer bottom surface of the light-emitting tube.

The electrode substrate 20 comprises an insulating support body 21 made from glass epoxy or the like as a foundation and a pair of electrodes 22X, 22Y arranged on a lower surface of the insulating support body 21. The insulating support body 21 supporting a plurality of light-emitting tubes 11 is placed on an upper surface thereof through an adhesive layer/bonding layer 23. The pair of electrodes 22X, 22Y has an electrode gap 24 as a discharge gap interposed therebetween and placed at a substantially central part of a longitudinal direction of the light-emitting tubes 11. The pair of electrodes 22X, 22Y is configured to be spread toward the both sides of the electrode gap 24, and has a pattern covering the light-emitting tubes 11 overall at the both sides of the electrode gap 24 (see FIG. 1B).

Figure 1B:
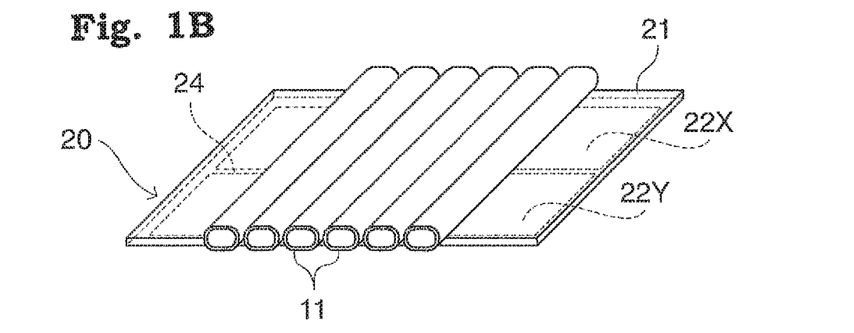
FIG. 1B illustrates a diagrammatic perspective view of a light-emitting tube array-type light source device.

FIG. 1B schematically illustrates a perspective view of a light-emitting tube array-type light source device including the plurality of gas discharge light-emitting tubes 11. The insulating support body 21 constituting the electrode substrate 20 has the plurality of light-emitting tubes 11 placed thereon in parallel to each other. The pair of electrodes 22X, 22Y has the electrode gap interposed therebetween to cross over the plurality of light-emitting tubes 11 overall. Each of electrodes 22X, 22Y has a pattern overall facing bottom surfaces of the light-emitting tubes 11. The pair of electrodes 22X, 22Y may be arranged on the upper surface of the insulating support 21.

Figure 1C:
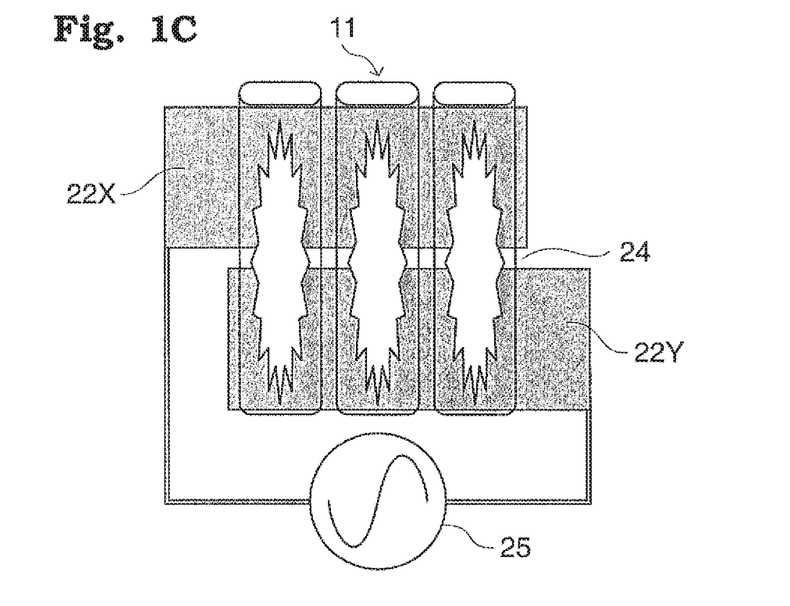
FIG. 1C illustrates a diagrammatic view of a drive circuit of the light-emitting tube array-type light source device.

FIG. 1C illustrates a structural view of a circuit to describe a drive principle of the light-emitting tube array-type light source device. An inverter power supply 25 applies an alternating voltage between the pair of electrodes 22X and 22Y at a peak voltage of 1,000 to 2,000 V and a frequency from 30 to 40 kHz. An initial discharge is generated at a discharge gap inside each light-emitting tube 11, which corresponds to the electrode gap 24 between the pair of electrodes 22X, 22Y, during an increasing process of a sine wave to be applied as an alternating drive voltage, and the discharge expands in a longitudinal direction of the light-emitting tubes with a subsequent increase of the sine wave voltage. This drive principle and a concrete drive circuit are described in detail in related art documents D1 and D3.

D1: JP WO 2016/125708 A1
D2: JP 2017-027912 A
D3: JP WO 2017/094483 A1

BRIEF SUMMARY OF THE INVENTION

Similar to other electronic devices, the above-described gas discharge-utilizing light-emitting tube array-type light source device itself cannot avoid heating up because the lighting operation changes a part of the supply power to heat. In the present circumstances, ultraviolet light conversion efficiency through the gas discharge and the ultraviolet phosphor is only a few percent. Therefore, if the supply power is increased in order to enhance emission luminance and emission power, a heating amount of the device proportionally increases accordingly. Overheating of the device leads to a decrease in luminous efficiency and makes it difficult to keep its luminance even.

Accordingly, the present invention has a main object of solving the heat generation-related problems of the light-emitting tube array-type light source device. The present invention also has an object of suppressing the overheating of the device and of providing the light-emitting tube array-type light source device whose luminance is even at its entire light-emitting surface and capable of maintaining stable performances for an extended period of time.

To put it simply, the present invention has an essential feature such that the electrode substrate has through-holes so as to partially expose bottom surfaces of the light-emitting tubes to the outside of the electrode substrate. This conception is based on a perception that even if the pair of electrodes extending on the back side surface of the light-emitting tube array partially has slit-like missing parts, discharge effects would not be affected.

Specifically, the light-emitting tube array-type light source device according to the present invention comprises: a plurality of gas discharge light-emitting tubes and an electrode substrate, the light-emitting tubes made of glass tubes and enclosing a discharge gas, the electrode substrate supporting the light-emitting tubes on an upper surface thereof in parallel to each other and having a pair of electrodes arranged on a one surface thereof, the pair of electrodes having an electrode gap interposed therebetween commonly across the light emitting tubes and spreading apart from each other on the both sides of the electrode gap, characterized in that the electrode substrate having through-holes allowing each light-emitting tube to be partially exposed downward.

It is desirable that the through-holes of the electrode substrate should be shaped like slits and should be parallel to the gap interposed between the pair of electrodes, which constructs the discharge gap in the gas discharge tube. However, if the through-holes do not prevent the gas discharge, the several through-holes may be provided with a dispersed arrangement in the form of a circle, a quadrangle, etc. The through-holes, that is, a plurality of slits functioning as ventilation holes may be placed so as to lay across the light-emitting tubes with a slit corresponding to the gap between the electrodes included in such slits.

Considering that the slits of the electrode substrate should not allow an unnecessary air discharge between the electrodes and the lower surfaces of the light-emitting tubes, it is important that a pattern of the pair of electrodes should be arranged in such a way that edges of the pattern get behind edges of the slits and do not face the lower surfaces of the light-emitting tubes.

The present invention has another aspect as follows: the electrode substrate supporting the light-emitting tube array comprising the plurality of gas discharge light-emitting tubes may have on its upper surface a pair of auxiliary electrodes connected to the pair of electrodes, the auxiliary electrodes being configured to be respectively arranged on both ends of the longitudinal direction of each of the light-emitting tubes. Moreover, a pair of trigger electrodes may be respectively placed at an upper surface of the electrode substrate which corresponds to proximity ends of the pair of electrodes forming the discharge gap of the electrode substrate so as to make an initial discharge easy. By adding the pair of auxiliary electrodes and the pair of trigger electrodes, the entire light-emitting surface can exhibit the uniform luminance characteristic and can enhance certainty and reliability of gas discharge performances.

The light-emitting tube array-type light source device according to the present invention can be used as a flat light source-type ultraviolet light source; and in this case, the "flat light source" includes not only light sources having a flat light-emitting surface but also light sources having a curved light-emitting surface that is optionally bendable such as a cylindrical surface. The "ultraviolet light source" means light sources of an entire range of ultraviolet light, such as ultraviolet light in UV-A, UV-B and UV-C frequency bands emitted from an ultraviolet phosphor and vacuum ultraviolet light emitted from the gas discharge itself.

By virtue of the present invention, every gas discharge light-emitting tube of the light-emitting tube array-type light source device can have sufficient heat dissipation effects through the through-holes of the electrode substrate. As a result, the light source device of a deep ultraviolet region is capable of preventing a decrease in luminance caused by the increased temperature and of maintaining stable operational performances for an extended period of time, and also is capable of expanding usage of the light-emitting tube array-type light source device characterized by being mercury-free to a medical field, a sterilization, disinfection and deodorization field, and an industrial field.

DESCRIPTION OF THE PREFERRED EMBODIMENTS

In the following, this invention will be described in detail through the use of the Embodiments illustrated in the drawings. These Embodiments are not to limit this invention.

Embodiment 1

Figure 2A:
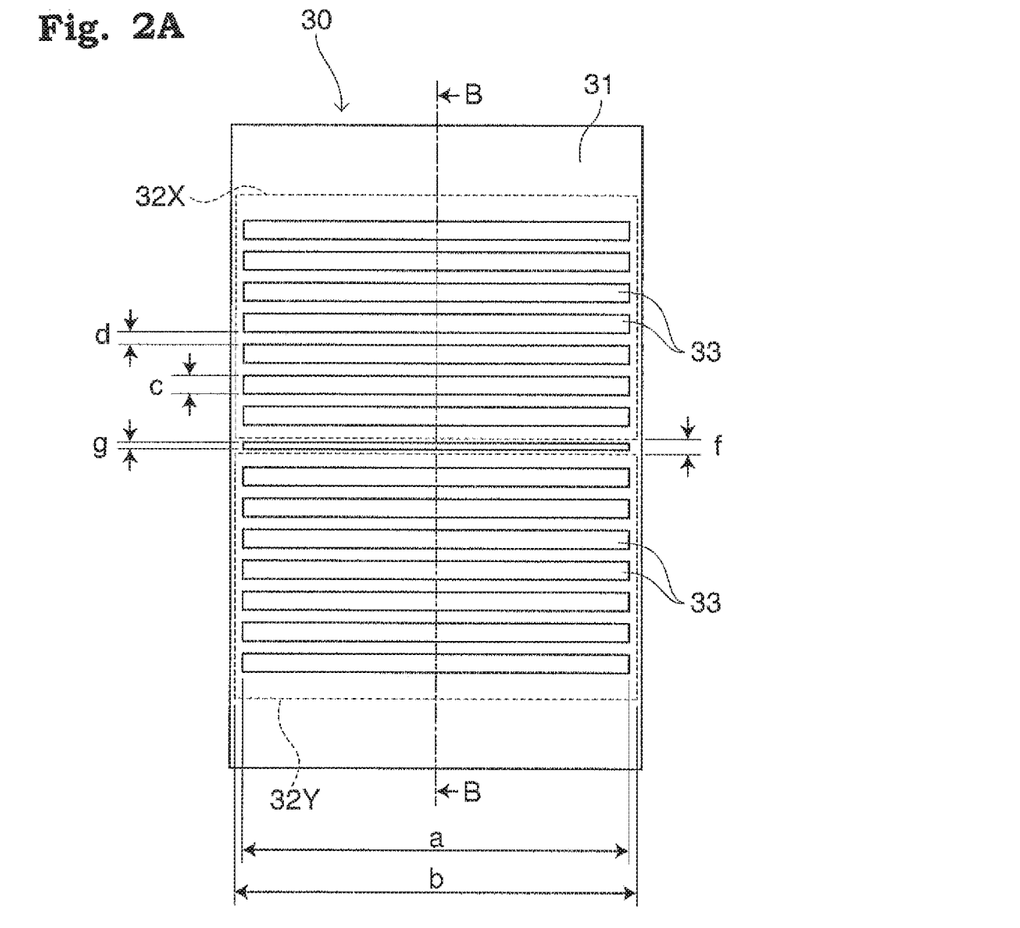
FIG. 2A illustrates a plan view indicating a structure of an electrode substrate in accordance with Embodiment 1 of the present invention.
Figure 2B:
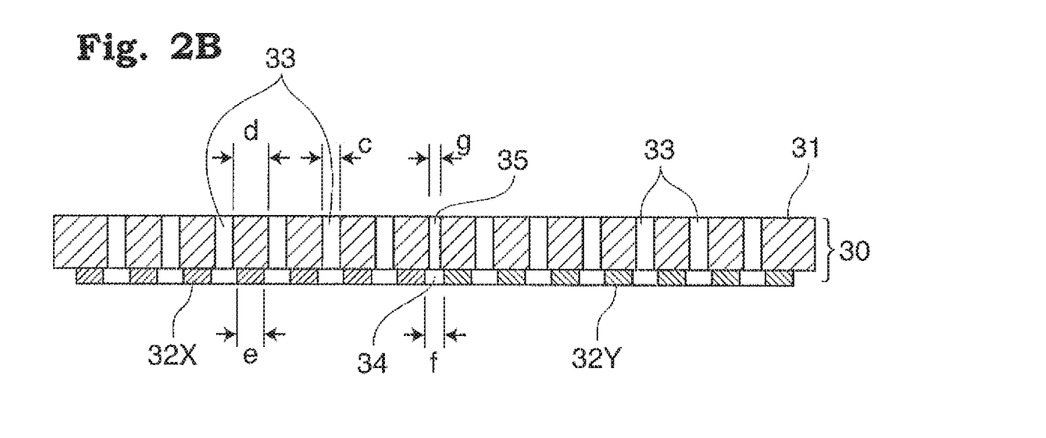
FIG. 2B illustrates an explanatory cross-section view of the electrode substrate.

FIG. 2A illustrates a plan view indicating a structure of an electrode substrate in accordance with Embodiment 1 of the present invention; and FIG. 2B illustrates a cross-section view along arrows B-B in FIG. 2A. An electrode substrate 30 includes an insulating support body 31 and a pair of electrodes 32X, 32Y formed on a lower surface of the insulating support body 31. The electrode substrate 30 has, as a feature of the present invention, a plurality of slits (through-holes) 33 that penetrate through the insulating support body 31 and the electrodes 32X, 32Y and are aligned in parallel to each other.

The insulating support body 31 is made of a glass epoxy substrate having a thickness of 1 mm or less, preferably about 600 to 800 µm. The pair of electrodes 32X, 32Y is formed by patterning a metallic conductor layer on a lower surface of the glass epoxy substrate, the metallic conductor layer being formed by subjecting copper or aluminum to a plating process, an evaporation coating process, or the like. Although not illustrated, the pair of electrodes 32X, 32Y is coated with an insulating film.

A plurality of slits 33 of the electrode substrate 30, which are the feature of the present invention, are placed in such a way as to be parallel to an electrode gap 34 interposed between the electrodes 32X, 32Y, which corresponds to the electrode gap 24 (illustrated in FIG. 1). Therefore, the pattern of the electrodes 32X, 32Y seem to be divided into a plurality of band patterns by these slits 33.

However a long-side length b of each of electrodes 32X, 32Y is designed to be longer than a longitudinal length a of the slits 33, and therefore the electrodes which seem to be divided by the slits 33 are configured to be electrically connected to each other at both ends of the slits 33 in which a ladder pattern is formed.

Needless to say, the pair of electrodes 32X, 32Y may have a pattern such that an electrode structure of the pair of electrodes depends on a pattern of the ventilation holes, and have bridges in such a way as to partially get across the slits 33 so that a drive current can easily flow through an electrode conductor on the bridge.

In an example wherein the slits are used as ventilation holes, when a light-emitting tube array-type flat light source device whose light-emitting area is 8 cm×6 cm (48 cm$^2$) is made, the plurality of slits 33 are provided with equally-spaced pitches through the insulating support body 31 on which the pair of electrodes 32X, 32Y are placed. As shown in FIGS. 2A and 2B, the slit 33 is 5 mm or less, preferably about 2 to 3 mm, in width c.

A width d between the adjacent slits is about 3 mm, and is configured to be wider than the slit width c (c<d). An electrode width e between the adjacent slits is also configured to be wider than the slit width c, but is configured to be narrower than the width d between the adjacent slits (c<e<d).

The electrode gap 34 is 5 mm or less in width f, and the width of about 3 mm is preferable. An electrode gap slit 35 is placed in such a way as to correspond to the electrode gap 34; and a width g of the electrode gap slit 35 is configured to be narrower than the gap width f (f>g). Therefore, the width of each slit of the pair of electrodes 32X, 32Y is slightly wider than the width of each slit of the substrate support body 31, and the pair of electrodes 32X, 32Y is configured to be hidden from each of the slits 33 and the slit 35.

Figure 3A:
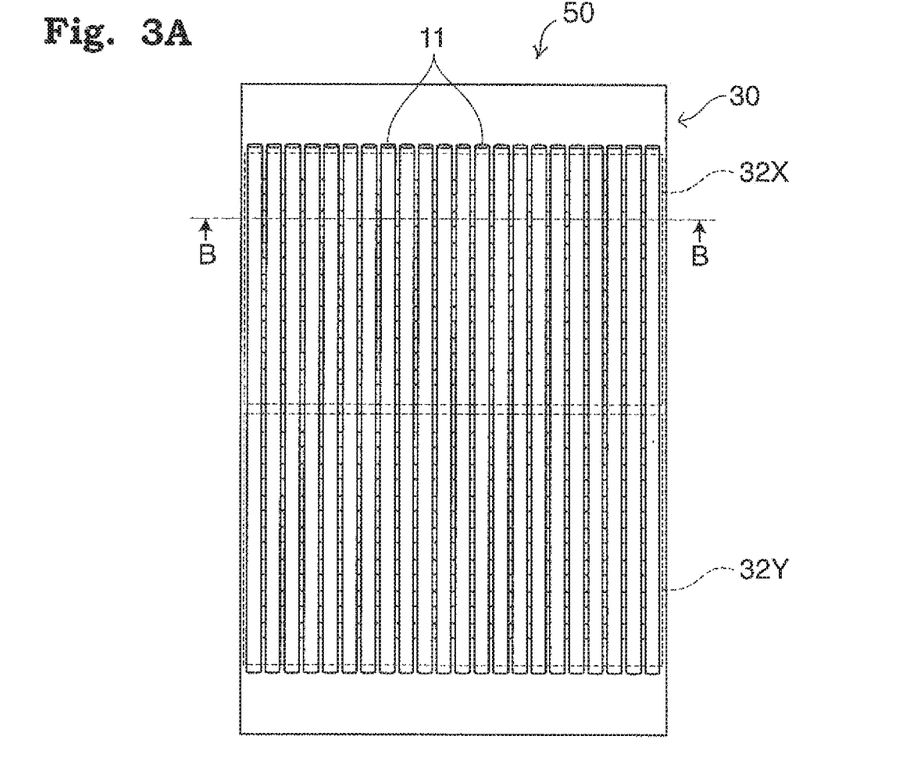
FIG. 3A illustrates a diagrammatic plan view of a light-emitting tube array-type light source device in accordance with Embodiment 1 of the present invention.
Figure 3B:
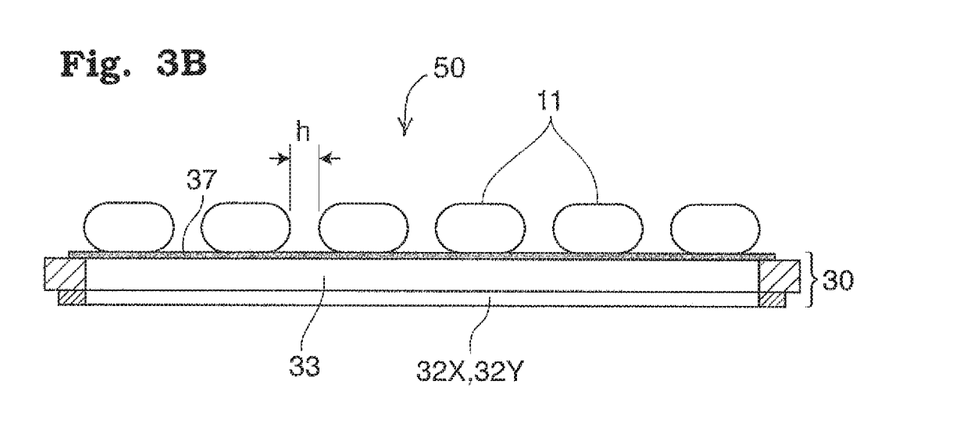
FIG. 3B illustrates a cross-section view of the light-emitting tube array-type light source device.

FIG. 3A illustrates a plan view indicating a structure of a light-emitting tube array-type light source device 50 having a gas discharge light-emitting tube array where a plurality of gas discharge light-emitting tubes are placed on the electrode substrate 30 of the present invention, for example, twenty-two gas discharge light-emitting tubes 11 are arranged in parallel to each other in this drawing; and FIG. 3B illustrates a cross-section view of the light-emitting tube array-type light source device, viewed along arrows B-B in FIG. 3A. Note that this cross-section view illustrates less light-emitting tubes 11 than those illustrated in the plan view for the convenience of drawing.

A basic structure of the gas discharge light-emitting tube 11 as a unit light-emitting element is the same as the gas discharge light-emitting tube 11 illustrated in FIG. 1(a).

Namely, each of the gas discharge light-emitting tubes 11 is composed of a thin tube made of borosilicate glass whose transverse cross-section is flat-oval or circular. The tube 11 made of the borosilicate glass has a thickness of 300 µm or less, preferably about 100 µm at a front side of the tube serving as a light emitting surface, to allow ultraviolet light to pass therethrough. Of course, the quartz glass may be used as a material of the thin tube. By the way, a flat light source having a light-emitting surface size of 8 cm×6 cm is formed by arranging on an upper surface of a 10 cm×6.2 cm electrode substrate 30 twenty-two light-emitting tubes 11 having a length (effective discharge length) of 8 cm, a long side outer diameter of 2 mm, and a short side outer diameter of 1 mm and having gaps h of 0.7 mm between the adjacent light-emitting tubes with an array pitch of 2.7 mm.

The plurality of light-emitting tubes 11 are supported through an adhesive/bonding layer 37 on the electrode substrate 30, which corresponds to the electrode substrate 20 illustrated in FIG. 1. The light-emitting tubes 11 pasted to the electrode substrate 30 through the adhesive/bonding layer 37 can be individually detached from the electrode substrate 30, and this is convenient for repairing or replacing the light-emitting tubes 11. It is important here that when the light-emitting tubes 11 are pasted, the slits 33, 35 of the electrode substrate 30, which function as ventilation holes, should not be covered with the adhesive/bonding layer 37 or the like.

In the light source device 50 of FIGS. 3A and 3B assembled as above, the light-emitting tubes 11 are placed in such a way that their bottom surfaces are exposed downward through the slits 33, 35 (see FIG. 2B) of the electrode substrate 30. Since there are also gaps h (see FIG. 3B) between the adjacent light-emitting tubes 11, the light-emitting tubes 11 that cross over the slits 33, 35 form ventilation holes between side surfaces of the adjacent light-emitting tubes 11 with the ventilation holes opened downward. Namely, the slits 33, 35 of the electrode substrate 30 come to function as partial heat-releasing passages for the light-emitting tubes 11.

Figure 4A:
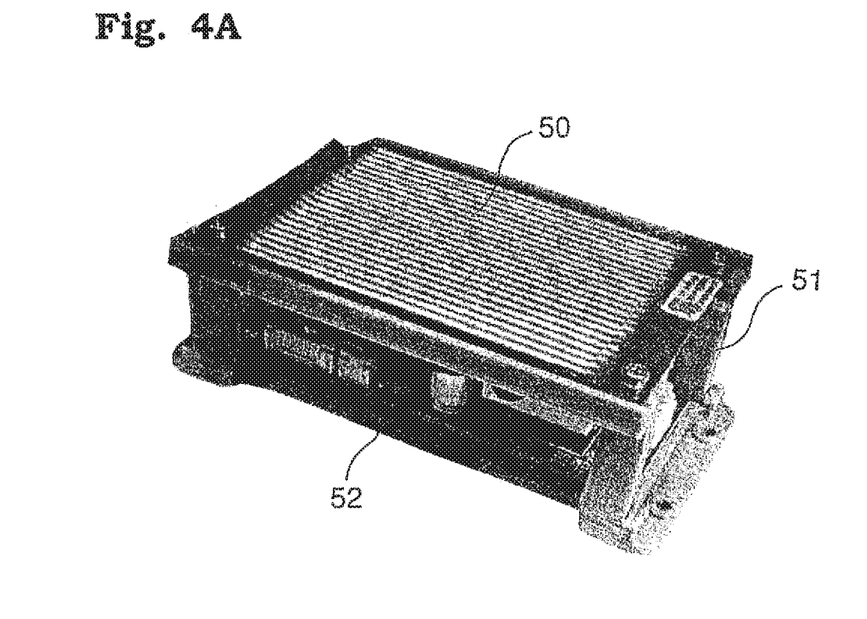
FIG. 4A shows a schematic perspective view of a light source module having the light-emitting tube array-type light source device of FIGS. 3A and 3B incorporated therein.
Figure 4B:
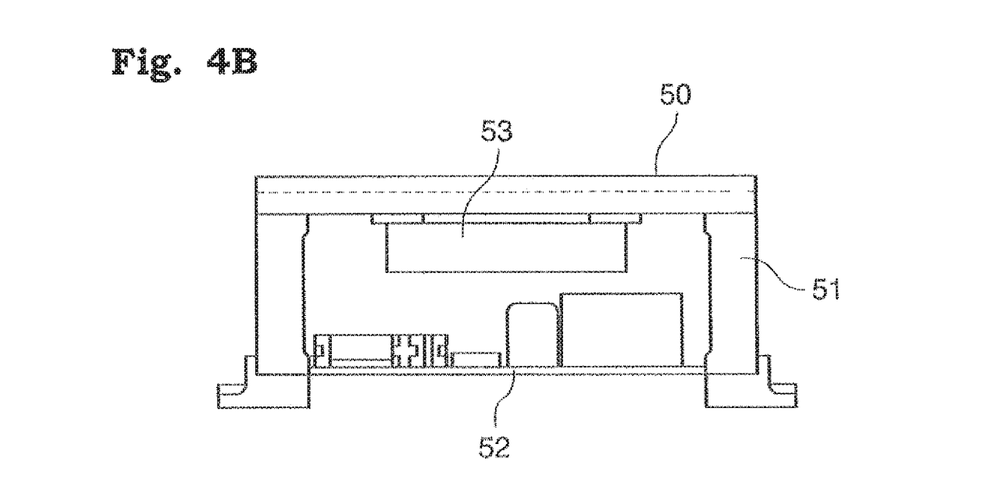
FIG. 4B illustrates an explanatory view of a structure of the light source module.

FIG. 4A shows a schematic perspective picture view of a light source module having the light-emitting tube array-type light source device 50 installed in a frame housing 51, and FIG. 4B illustrates an explanatory view of a structure of the module viewed from its side. An electrode substrate of the light source device 50 is screwed to an upper frame of the frame housing 51, and a circuit board 52 for drive circuits is fixed to a lower part of the frame housing 51. A cooling fan 53 installed under the upper frame in such a way that the cooling fan 53 is placed opposite to a lower surface of the electrode substrate of the light source device 50. A light-emitting surface of the light source device 50 may be optionally coated with a protection film (not illustrated), having an ultraviolet light transmission function.

The circuit board 52 for driving circuits is equipped with circuit components, such as a switching transistor, a condenser, and a boosting transformer, that constitute the inverter power supply 25 as disclosed in the above-mentioned document D3. The driving circuit on the circuit board 52 is adapted to convert, for example, a DC input voltage of 12 V into a sine wave alternating voltage of peak-to-peak 2,000 V at a frequency from about 30 to 40 kHz and to apply the sine wave alternating voltage between the electrodes of the light source device 50.

The circuit board 52 for driving circuits is also equipped with a burst control circuit that intermittently controls the application of an alternating driving voltage to the light source device 50 and with a circuit that controls a duty ratio of the alternating driving voltage.

The cooling fan 53 is rotated together with a lighting operation of the light source device 50. When the cooling fan rotates forward, cooling airflow expels heat upward, which is generated from the light-emitting tubes 11, through the slits 33, 35 of the electrode substrate 30 (see FIGS. 2A and 2B) of the light source device 50.

When the cooling fan 53 is rotated backward, cooling airflow is sucked from the front side of the light source device 50 through the slits 33, 35; and heat generated from the light-emitting tubes 11 is discharged downward. The suction method that rotates the fan 53 backward is generally superior in heat dissipation effects to the other method, although such effects depend on the configuration of the entire module or the structure of the frame housing 51.

In a case where the alternating drive voltage is applied between the pair of electrodes 32X, 32Y in the light source module as above, an electric field distribution in a longitudinal direction of the light-emitting tubes 11 becomes unsteady (irregular) because the electrodes 32X, 32Y are divided by the slits 33. However, if the slit width of the electrodes 32X, 32Y is 5 mm or less, an electric field is sufficiently induced in slit corresponding parts inside the light-emitting tubes through a tube wall of the glass tubes 10 which is a dielectric, and therefore there will be almost no impact on gas discharge throughout the tubes.

Embodiment 2

Figure 5:
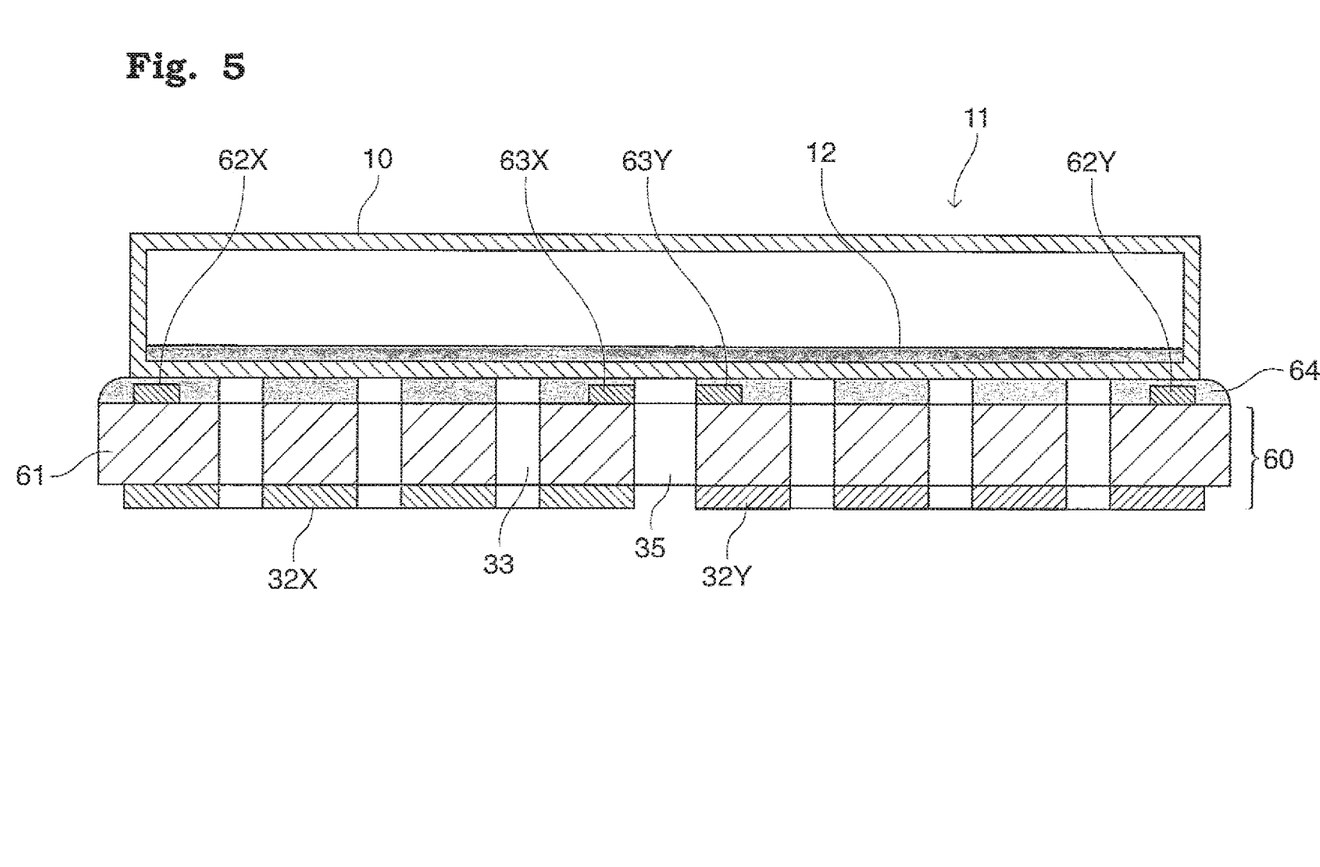
FIG. 5 illustrates an explanatory cross-section view of a light-emitting tube array-type light source device in accordance with Embodiment 2 of the present invention.

FIG. 5 illustrates an explanatory transverse cross-section view of a light-emitting tube array-type light source device including an electrode substrate 60 in Embodiment 2 of the present invention. The pair of electrodes 32X, 32Y is placed on a lower surface of an insulating support body 61 that functions as a foundation of the electrode substrate 60; and the slits 33, 35 are formed in the electrode substrate 60 through the pair of electrodes 32X, 32Y and the insulating support body 61, in the same way as in the above-described Embodiment 1.

A feature of this Embodiment 2 is that a pair of auxiliary electrodes 62X, 62Y are placed at positions corresponding to both ends of the light-emitting tubes 11, respectively, and are placed on an upper surface of the electrode substrate 60. A pair of trigger electrodes 63X, 63Y are respectively placed at positions corresponding to proximity ends of the pair of electrodes 32X, 32Y forming the discharge gap therebetween.

The pair of auxiliary electrodes 62X, 62Y and the pair of trigger electrodes 63X, 63Y are covered with an insulating bonding/adhesive layer 64 that is about 200 μm in thickness and is to paste the light-emitting tubes 11 to the electrode substrate, and therefore these electrodes are not in direct contact with the glass tubes 10 of the light-emitting tubes 11. Needless to say, this bonding/adhesive layer 64 covers the electrodes in such a way as not to cover the slits 33, 35.

The auxiliary electrodes 62X, 62Y placed respectively at the both ends of the light-emitting tubes 11 are respectively connected to the corresponding electrodes 32X, 32Y at the lower surface of the insulating support body 61 through through-hole conductors (not illustrated). The trigger electrodes 63X, 63Y are also respectively connected to the electrodes 32X, 32Y at the lower surface of the insulating support body 61 through the through-hole conductors (not illustrated).

The pair of auxiliary electrodes 62X, 62Y acts to enhance electric fields at the both ends of the light emitting tube 11 and compensate for a decrease in luminance at the both ends of the light-emitting tubes 11. The pair of trigger electrodes 63X, 63Y more effectively ensures that an initial discharge certainly generates at the electrode gap slit 35 upon lighting. Depending on a desired size and/or emission intensity of the light-emitting surface, at least one of the pair of auxiliary electrodes 62X, 62Y and the pair of trigger electrodes 63X, 63Y may be properly added.

The pair of auxiliary electrodes 62X, 62Y or the pair of trigger electrodes 63X, 63Y properly added fulfills its functions regardless of the presence or absence of the ventilation slits 33, 35 in the electrode substrate 30 or the electrode substrate 60. On the other hand, the electrode substrate 30 or the electrode substrate 60 which increases heat dissipation effects thanks to the slits 33, 35 is capable of enhancing further reliability of its gas discharge performance and light-emitting performance.

Embodiment 3

Figure 6A:
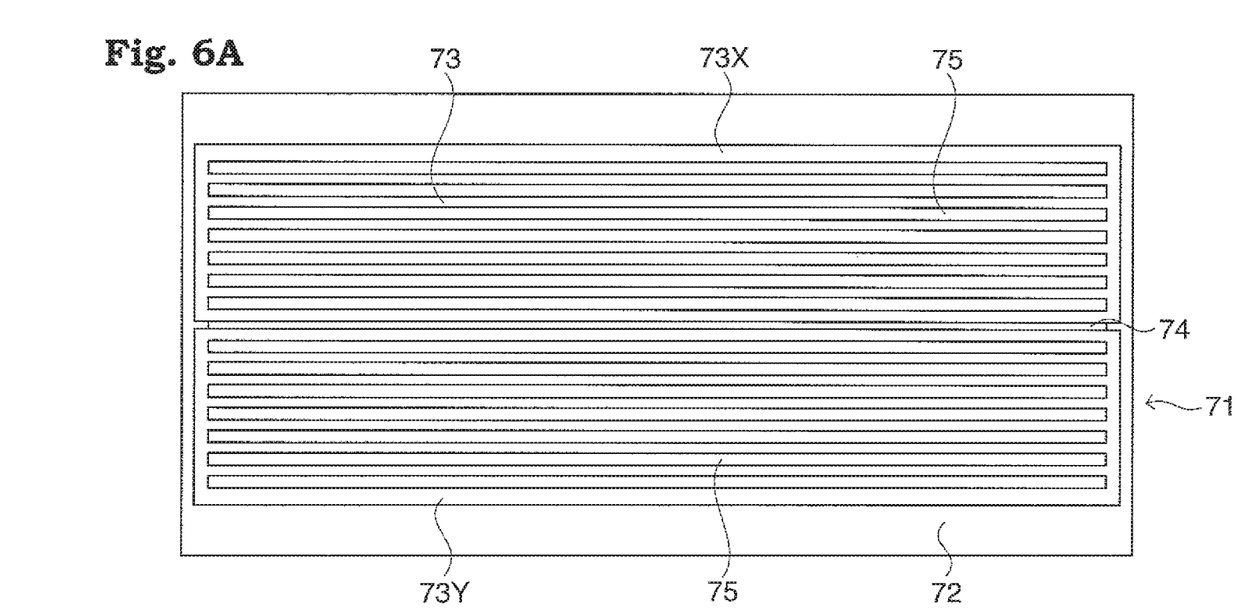
FIG. 6A illustrates a diagrammatic plan view indicating a structure of a flexible light-emitting tube array-type light source device in accordance with Embodiment 3 of the present invention.
Figure 6B:
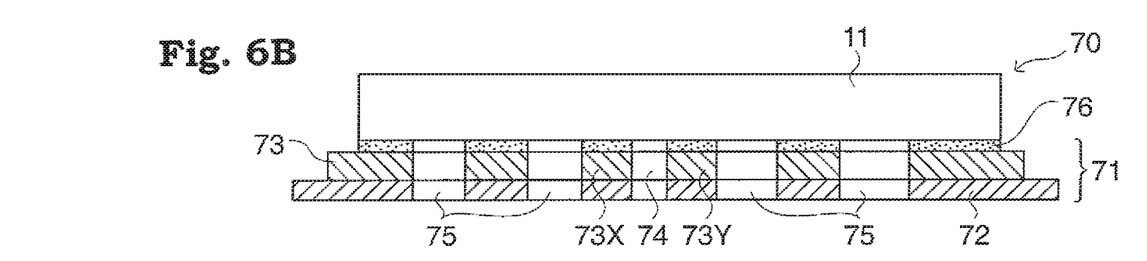
FIG. 6B illustrates a transverse cross-section view of the flexible light-emitting tube array-type light source device.

FIG. 6A illustrates a plan view indicating a structure of an electrode substrate of a flexible light-emitting tube array-type light source device in accordance with Embodiment 3 of the present invention; and FIG. 6B illustrates a diagrammatic cross-section view of the electrode substrate having light-emitting tubes placed thereon. Note that the number, widths, etc. of slit-like ventilation through-holes of the electrode substrate illustrated in the cross-section view of FIG. 6B do not precisely correspond to those illustrated in the plan view of FIG. 6A for the purpose of making the drawings simplified.

A light source device 70 in accordance with Embodiment 3 is characterized by its flexible structure. An electrode substrate 71 comprises a polyimide-based film substrate 72, which is a heat-resistant resin film known as, for example, Kapton (trade name), and an electrode conductor layer 73 formed of a copper foil or the like and laminated on the film substrate 72. The electrode conductor layer 73 is divided into a pair of electrodes 73X, 73Y having an electrode gap 74 interposed therebetween, the electrode gap 74 constructing a discharge gap in the light emitting tube 11. The electrodes 73X, 73Y has the electrode gap 74 that penetrates through the film substrate 72 and also has a plurality of slit-like ventilation through-holes 75 that are aligned in parallel with the gap 74 and penetrate through the film substrate 72, and the electrode gap 74 also functions as a ventilation through-hole. Since the electrode 73X and the electrode 73Y are completely divided by the electrode gap 74, the film substrate 72 may not have any through-slit in an area corresponding thereto in consideration of an overall strength.

The electrode conductor layer 73 of the electrode substrate 71 has a plurality of gas discharge light-emitting tubes 11 placed thereon, the gas discharge light-emitting tubes being arranged in parallel to each other and spaced out at regular intervals and crossing over the electrode gap 74 that is to construct the discharge gap. As illustrated in the cross-section view of FIG. 6B, the gas discharge light-emitting tubes 11 are supported by a silicone resin-based adhesive layer or bonding layer 76 as an insulating layer placed on the electrode conductor layer 73. The film substrate 72 is about 50 μm in thickness, and by using a copper foil having a thickness of about 200 μm as the electrode conductor layer 73, the electrode substrate 71 becomes 300 μm or less in thickness. The electrode substrate 71 may be formed of a three-layer film such that a metallic foil or a thin metallic sheet as the electrode conductor layer 73 is sandwiched between polyimide-based resin films, and the ventilation through-holes 75 can be formed by punching processing in a predetermined arrangement. Alternatively, a pattern of the pair of electrodes 73X, 73Y is formed by using a thin copper sheet whose both sides are coated with insulating films, and the gas discharge light-emitting tubes 11 may be arranged as the tubes lie across the pair of electrodes 73X, 73Y. Another exemplary structure is formed in such a way that the film substrate 72 is coated with a metallic conductor film to form a laminate substrate; and then the laminate substrate is subjected to laser processing or cutting processing to form a predetermined pattern of ventilation through-holes on the laminate substrate.

In this case, it is desirable that the entire electrode substrate or the through-hole parts should be coated with a resin for safety reasons since edges of the electrodes are exposed due to the forming process of the through-holes.

Therefore, in a case where the gas discharge light-emitting tubes 11 having a tube diameter of 1 mm are arranged on the electrode conductor layer 73 to be embedded in the about 150-micrometer-thick bonding layer 76, the flexible light-emitting tube array-type light source device 70 can be formed whose entire thickness is about 1.5 mm. Namely, this film-type flat light source 70 is flexible in the array direction of the gas discharge light-emitting tubes 11, enabling the light source itself to be cylindrical or the light-emitting surface to be curved or tortuous.

Example 1

Figure 7A:
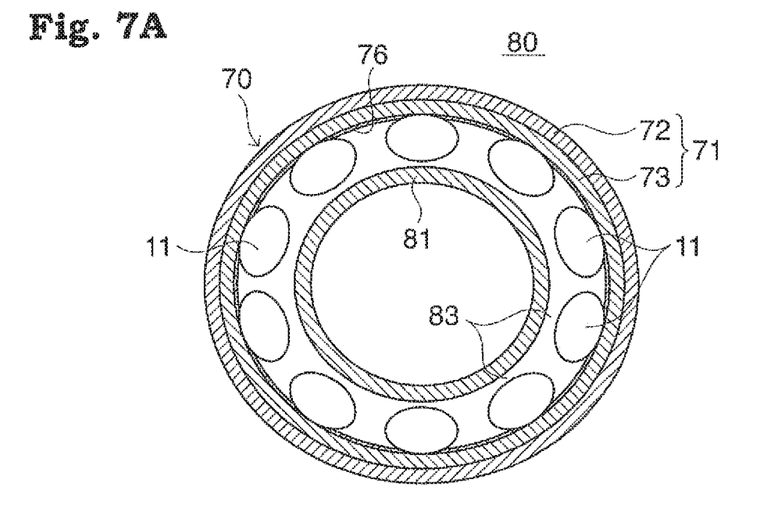
FIG. 7A illustrates a transverse cross-section view indicating a structure of a running water sterilization device as Applied Example 1 using a light-emitting tube array-type light source device according to the present invention.
Figure 7B:
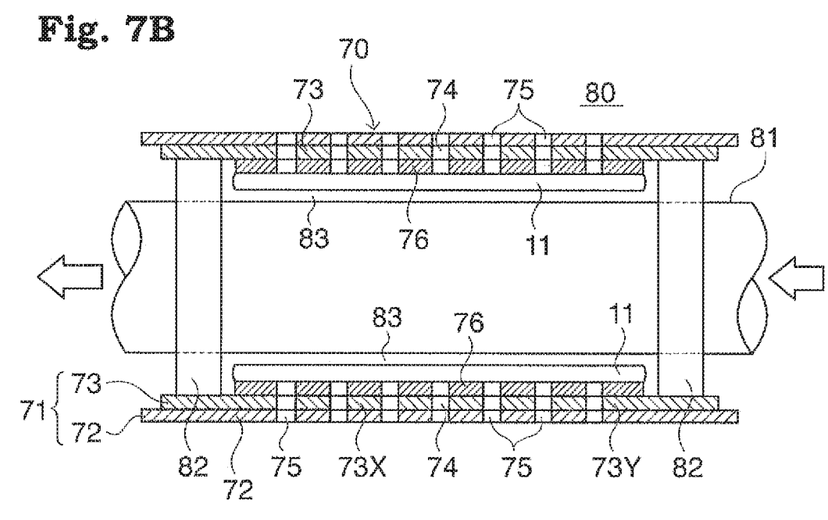
FIG. 7B illustrates a longitudinal cross-section view of the running water sterilization device.

FIG. 7A diagrammatically illustrates a transverse cross-section view of a running water sterilization device 80 as a fluid treatment device using the flexible light-emitting tube array-type light source device 70 described in Embodiment 3, and FIG. 7B illustrates a longitudinal cross-section view of the running water sterilization device 80. An ultraviolet light-permeable running water pipe 81, which is a main component of the device 80, is equipped with a pair of spacer rings 82 made of an insulating resin and spaced at a predetermined distance. The electrode substrate 71 constituting the flexible light-emitting tube array-type light source device 70 lies astride the spacer rings 82; and both ends of the electrode substrate 71 are wrapped around the spacer rings to be attached to the spacer rings 82, respectively, with use of a double-faced adhesive tape or the like (not illustrated). An outer diameter of the spacer ring 82 is configured to be larger than the sum of diameters of two light-emitting tubes 11 facing each other across the running water pipe 81 and an outer diameter of the running water pipe 81. As a result, there exists an air ventilating space 83 between the light-emitting tubes 11 each and the running water pipe 81 in the light source device 70 that is rolled up and assembled in a cylindrical shape.

The running water pipe 81 is made of an ultraviolet light-permeable quartz tube or a PFA tube made from a fluorine-based resin. This running water pipe 81 is connected through gaskets (not illustrated) to an inlet tube and an outlet tube at its both ends, respectively. The entire structure illustrated in FIGS. 7A and 7B together with a drive circuit unit and a control circuit unit (not illustrated) is contained in a housing, and a cooling fan and an exhaust port are configured to be arranged opposite to each other through the running water pipe 81 wrapped with the light source device 70, making the running water sterilization device 80 completed. In a case where a sterilization device having a large flow volume is prepared by using a large-diameter running water pipe, the pipe is wrapped with a plurality of light source devices 70 in a longitudinal direction of the pipe in order to obtain sufficient disinfection effects. Namely, by wrapping two or three light source devices 70 around the pipe in series, an ultraviolet irradiation area is lengthened, and the disinfection effects are enhanced.

In the structure above, by lighting the plurality of gas discharge light-emitting tubes 11 of the light source device 70, running water in the running water pipe 81 is irradiated with ultraviolet light from an entire circumference of the pipe and is subjected to a disinfection treatment. In this case, if the cooling fan (not illustrated) is operated, and cooling air is blown to a lateral side of the running water pipe 81, then the cooling air flows to an exhaust port through the ventilation through-holes 75, the gaps between the adjacent light-emitting tubes 11 of the electrode substrate 71 of the light source device 70 and the ventilating space 83 between the light-emitting tubes 11 and the running water pipe 81, and thereby cools the light-emitting tubes 11 effectively. Namely, the flexible light-emitting tube array-type light source device according to the present invention is capable of preventing the light-emitting tubes 11 from being heated excessively because the back side of the light source device 70 wrapped around the running water pipe 81 is not blocked in ventilation, that is, the cooling airflow passing through the ventilation through-holes 75 comes in direct contact with the light-emitting tubes 11. In this case, if the cooling fan is driven in such a way as to suck the airflow, a tube wall of the running water pipe 81 is likely to become dirty, and therefore it is preferable that the cooling air should be blown to the light source device 70 wrapped around the running water pipe 81.

Example 2

Figure 8:
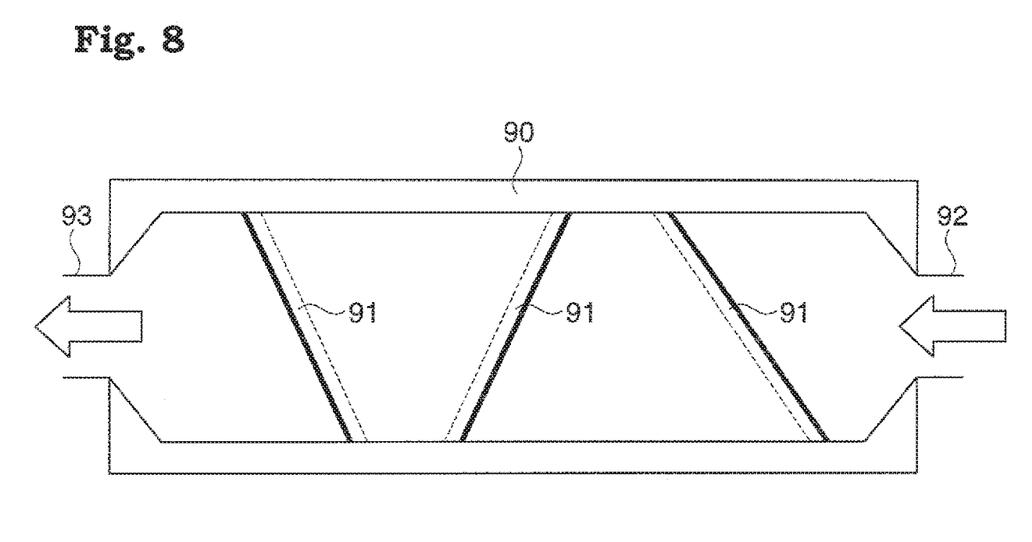
FIG. 8 illustrates a schematic view indicating a structure of an air-deodorizing device as Applied Example 2 using a light-emitting tube array-type light source device according to the present invention.

FIG. 8 illustrates a schematic view indicating a diagrammatic structure of an air-deodorizing device as another fluid treatment device using the light-emitting tube array-type light source device in accordance with Embodiment 1. It has been well known that vacuum ultraviolet light and ultraviolet light within a deep ultraviolet region have an air-deodorizing ability and a compound-decomposing ability. In Example 2 illustrated in FIG. 8, three ultraviolet light-emitting flat light sources 91 using an electrode substrate having through-slits are arranged in a deodorant box 90 in such a way that the ultraviolet light-emitting flat light sources are configured to tilt as their inclination angles change alternately and to cross a flow path diagonally. Each ultraviolet light-emitting flat light source 91 is representatively illustrated with a heavy line and a dashed line, but it has the same structure as the light-emitting tube array-type light source device in accordance with Embodiment 1 illustrated in FIG. 3. Namely, the plurality of gas discharge light-emitting tubes that emit ultraviolet light are arranged on the electrode substrate having slits in such a way as to have gaps between the adjacent tubes, forming a structure such that a plurality of air passages is shaped like a lattice by the gaps between the adjacent tubes and the slits of the electrode substrate.

Gas, such as air to be treated, blown through an inlet port 92 of the deodorant box 90 passes through the lattice-like air passages of each ultraviolet light-emitting flat light source 91 in the deodorant box 90, and is discharged from an outlet port 93. The air brought into the deodorant box 90 passes through a space for the ultraviolet irradiation and is deodorized effectively by lighting each of the ultraviolet light-emitting flat light sources 91. By making an inner wall surface of the deodorant box 90 a mirror surface, the ultraviolet light reflected from the inner wall surface can be used as irradiation light, enhancing deodorant effects.

Other Modified Embodiments

In Embodiments 1 and 2, the ventilation holes perforated through the electrode substrate are shaped like slits across the light-emitting tube array. However, since the ventilation holes according to the present invention may be configured such that bottom surfaces of the light-emitting tubes are partially exposed to the cooling air, the ventilation holes in the form of a circle, an ellipse, etc. may be dispersedly arranged, as long as missing parts of the electrode substrate do not affect the discharge performance.

The pair of electrodes formed on the lower surface of the electrode substrate is coated with an insulating film in the same way as on a conventional printed circuit board. Alternatively, the electrode substrate may have a three-layer structure such that the conductor layer is sandwiched between two insulating substrates.

Another aspect is that an electrode substrate having a pair of electrodes placed on an upper surface of a rigid insulating support body is prepared, and light-emitting tubes may be arranged on an insulating layer functioning as an adhesive/bonding layer placed on the electrode substrate. In any case, the electrode substrate is provided with a plurality of through-holes for releasing heat that partially expose the bottom surfaces of the light-emitting tubes, and the pair of electrodes has a pattern where each electrode is electrically connected and integrated around the through-holes.

Another aspect is that an electrode substrate functioning as a pair of electrodes may be formed of thin copper sheets having an electrode pattern where through-slits are formed. In this case, a plurality of light-emitting tubes are placed on the both sides of the electrode copper sheets having a gap to construct a discharge gap interposed therebetween; and the light-emitting tubes are spaced out at predetermined intervals and arranged in a direction to bridge the gap, forming a double-sided light-emitting flat light source having lattice-like air passages. The double-sided light-emitting ultraviolet light source with the air passages and the light-emitting tubes placed on the both sides of the electrode substrate is suitable for the deodorizing device of the above-described Example 2.

The present invention is suitable as the deep ultraviolet light-emitting flat light source. However, this light source may have light-emitting tubes having a green and blue-visible phosphor layer instead of the ultraviolet phosphor layer 12 (see FIG. 1A), forming a light-emitting surface by a combined light-emitting tube array comprising ultraviolet light-emitting tubes and visible light-emitting tubes, and thereby, an emission wavelength region may be optionally added. The pair of electrodes may be divided at every emission wavelength area of the light-emitting tube array, making the light source selectively operable.

REFERENCE SIGNS LIST

10: glass tube
11: gas discharge light-emitting tube
12: ultraviolet phosphor layer
20: electrode substrate
21: insulating support body
22X, 22Y: electrodes
23: adhesive/bonding layer
24: electrode gap
25: inverter power supply
30: electrode substrate
31: insulating support body
32X, 32Y: electrodes
33: slit
34: electrode gap
35: electrode gap slit
37: adhesive/boding layer
50: light-emitting tube array-type light source device
51: frame housing
52: circuit board for drive circuits
53: cooling fan
60: electrode substrate
61: insulating support body
62X, 62Y: auxiliary electrodes
63X, 63Y: trigger electrodes
64: adhesive/bonding layer
70: flexible light-emitting tube array-type light source device
71: electrode substrate
72: film substrate
73: electrode conductor layer
73X, 73Y: electrodes
74: electrode gap
75: ventilation through-hole
76: bonding layer
80: running water sterilization device
81: running water pipe
82: spacer ring
83: ventilating space
90: deodorant box
91: ultraviolet light-emitting flat light source
92: inlet port
93: outlet port

What is claimed is:

1. A light-emitting tube array-type light source device comprising: an electrode substrate including an insulating support and a pair of electrodes provided on a surface of the insulating support with a gap constituting a discharge gap; and a plurality of gas discharge light-emitting tubes arranged on the other surface of the insulating support and arranged in parallel to each other across the gap between the pair of electrodes,
wherein the electrode substrate has a plurality of through-holes which penetrate through the insulating support and the pair of electrodes to partially expose bottom surfaces of the light-emitting tubes.

2. The light-emitting tube array-type light source device of claim 1, wherein the through-holes have a pattern of a plurality of slits placed in parallel to the electrode gap.

3. The light-emitting tube array-type light source device of claim 2, wherein the pair of electrodes has an electrode pattern where a width of the pair of electrodes in a longitudinal direction of the slits is longer than a length of each slit, and each electrode is electrically connected in at least one end part of the adjacent slits.

4. The light-emitting tube array-type light source device of claim 2, wherein an electrode pattern is configured such that a width between the adjacent slits is wider than a width of each slit.

5. The light-emitting tube array-type light source device of claim 2, wherein the insulating support includes a slit in a part corresponding to the electrode gap, whose width is narrower than the electrode gap.

6. The light-emitting tube array-type light source device of claim 2, wherein a space is interposed between the adjacent light-emitting tubes arranged in parallel to each other; and thereby a plurality of ventilation holes is formed by adjacent side surfaces of the light-emitting tubes and by the slits formed in the electrode substrate and laying across the light-emitting tubes.

7. The light-emitting tube array-type light source device of claim 1, wherein the light-emitting tube has an ultraviolet light-emitting phosphor layer placed on an inner bottom surface thereof, the ultraviolet light-emitting phosphor layer emitting light within an ultraviolet region when excited by gas discharge light.

8. The light-emitting tube array-type light source device of claim 1, further comprising:
    a circuit board for driving the light-emitting tube array-type light source device, and
    a cooling fan provided under the light source device to cool the light-emitting tubes through the through-holes as ventilation holes of the electrode substrate,
    wherein the light source device, the circuit board, and the cooling fan are contained in one frame housing.

9. A light-emitting tube array-type light source device comprising:
    a gas discharge light-emitting tube array and an electrode substrate,
    the gas discharge light-emitting tube array comprising a plurality of gas discharge light-emitting tubes made of thin glass tubes and enclosing a discharge gas,
    the electrode substrate supporting the light-emitting tube array on an upper surface thereof and having a pair of electrodes on a lower surface thereof,
    the pair of electrodes having a gap interposed therebetween across the light-emitting tubes and being spaced apart by the gap so as to be respectively spread out in opposite directions from the gap,
    the electrode substrate having a plurality of through-holes allowing the light-emitting tubes to be partially exposed,
    the electrode substrate having a pair of trigger electrodes on an upper surface thereof, the trigger electrodes placed at proximity ends of the pair of electrodes to face each other and respectively connected to the electrodes.

10. The light-emitting tube array-type light source device of claim 9, wherein the electrode substrate has a pair of auxiliary electrodes on an upper surface thereof, the auxiliary electrodes respectively arranged on both ends of a longitudinal direction of the light-emitting tubes and respectively electrically connected to the electrodes.

11. A light-emitting tube array-type light source device comprising:
    an electrode substrate having a pair of electrodes with a gap constituting a discharge gap interposed therebetween; and a plurality of gas discharge light-emitting tubes arranged on the electrode substrate in parallel to each other across the gap between the pair of electrodes,
    wherein the electrode substrate has a plurality of through-holes partially exposing bottom surfaces of the gas discharge light-emitting tubes, and the pair of electrodes having a pattern electrically connected around the through-holes.

12. A light-emitting tube array-type light source device comprising:
    a plurality of gas discharge light-emitting tubes and a flexible electrode substrate,
    the light-emitting tubes being made of thin glass tubes and enclosing a discharge gas,
    the flexible electrode substrate having the light-emitting tubes on an upper surface thereof, the light-emitting tubes being arranged in parallel to each other and spaced apart at a predetermined interval,
    wherein the flexible electrode substrate comprises a pair of electrodes having a gap constituting a discharge gap interposed therebetween across the light-emitting tubes and being spaced apart by the gap so as to be spread out in opposite directions from the gap, and also comprises a plurality of open through-holes partially exposing bottom surfaces of the light-emitting tubes.

13. The light-emitting tube array-type light source device of claim 12, wherein the electrode substrate has a laminate structure comprising an insulating resin film as a film substrate and an electrode conductor layer laminated on the film substrate; and the open through-holes penetrate through the laminated film substrate and electrode conductor layers.

\* \* \* \* \*